United States Patent [19]

Missbach

[11] Patent Number: 5,338,746
[45] Date of Patent: Aug. 16, 1994

[54] THIOSEMICARBAZONIC ACID ESTERS

[75] Inventor: Martin Missbach, Rheinfelden, Switzerland

[73] Assignee: Ciba-Geigy Corporation, Ardsley, N.Y.

[21] Appl. No.: 121,973

[22] Filed: Sep. 15, 1993

Related U.S. Application Data

[63] Continuation of Ser. No. 66,814, May 24, 1993, abandoned.

[30] Foreign Application Priority Data

Jun. 3, 1992 [CH]  Switzerland ............... 01-777/92-1

[51] Int. Cl.$^5$ ............... A61K 31/425; C07D 277/04
[52] U.S. Cl. ............... 514/369; 548/147; 548/184
[58] Field of Search ............... 548/147, 184; 514/369

[56] References Cited

U.S. PATENT DOCUMENTS 5,136,037  8/1992  Hrib et al. ............... 548/147
5,229,405  7/1993  Feige et al. ............... 514/369

FOREIGN PATENT DOCUMENTS 0508955  10/1992  European Pat. Off. ............... 514/369
2035419   1/1971  Fed. Rep. of Germany ............... 514/369
1325061   8/1973  United Kingdom ............... 514/369

OTHER PUBLICATIONS

CA117(11): 111422t N-Bis(Methylthio)Methylene Derivatives . . . Sulfonamides, Tominaga et al., 1992.
Chem Abst. vol. 61, No. 10, Nov. 9, 1964, Abst. No. 12007g–12008a Japan 10,345 ('64) 2,4-Thiazolidinedione Derivatives–Hashimoto.

Primary Examiner—Robert W. Ramsuer
Assistant Examiner—Joseph K. McKane
Attorney, Agent, or Firm—Irving M. Fishman; Karen G. Kaiser

[57] ABSTRACT

The invention relates to novel thiosemicarbazonic acid esters of formula I

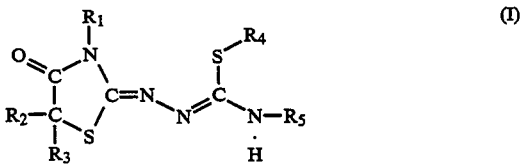

wherein
 $R_1$ and $R_5$ are lower alkyl, lower alk-2-en-1-yl or lower alk-2-yn-1-yl,
 $R_2$ and $R_3$ independently of one another are hydrogen or lower alkyl or together are lower alkylidene, and
 $R_4$ is lower alkyl, lower alkoxy, lower alk-2-en-1-yl, lower alk-2-yn-1-yl, aryl-lower alkyl, aryl-lower alkenyl or lower alkoxycarbonyl-lower alkyl, and to the salts and tautomeric compounds and double-bond isomers thereof, to processes for the preparation of the said compounds, to pharmaceutical compositions comprising them and to their use in the treatment of rheumatoid type diseases.

8 Claims, No Drawings

THIOSEMICARBAZONIC ACID ESTERS

This application is a continuation, of application Ser. No. 08/066,814, filed May 24, 1993 now abandoned.

The invention relates to novel thiosemicarbazonic acid esters of formula I

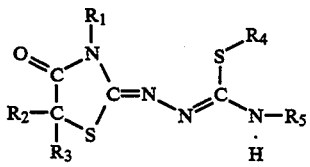

wherein
$R_1$ and $R_5$ are lower alkyl, lower alk-2-en-1-yl or lower alk-2-yn-1-yl,
$R_2$ and $R_3$ independently of one another are hydrogen or lower alkyl or together are lower alkylidene and
$R_4$ is lower alkyl, lower alkoxy, lower alk-2-en-1-yl, lower alk-2-yn-1-yl, aryl-lower alkyl, aryl-lower alkenyl or lower alkoxycarbonyl-lower alkyl,
and to the salts and tautomeric compounds and double-bond isomers thereof, to processes for the preparation of the said compounds, to pharmaceutical compositions comprising them and to their use as active ingredients in medicaments.

Hereinbefore and hereinafter, "lower" radicals and compounds are to be understood as being, for example, those having up to and including 7, preferably up to and including 4, carbon atoms (C atoms).

Lower alk-2-en-1-yl is, for example, $C_3$–$C_5$alk-2-en-1-yl, such as especially allyl, methallyl or dimethylallyl.

Lower alk-2-yn-1-yl is, for example, $C_3$–$C_5$alk-2-yn-1-yl, such as especially prop-2-yn1-yl or but-2-yn-1-yl.

Lower alkyl is, for example, $C_1$–$C_4$alkyl, such as methyl, ethyl, propyl or butyl.

Lower alkylidene is, for example, $C_1$–$C_4$alkylidene, such as especially methylene or ethylidene.

Lower alkoxy is, for example, n-propoxy, isopropoxy, n-butoxy or tert-butoxy, preferably ethoxy, and especially methoxy.

Aryl—in combined terms such as aryl-lower alkyl or aryl-lower alkenyl—is, for example, phenyl or naphthyl, such as 1- or 2-naphthyl, or substituted phenyl or naphthyl, such as phenyl or naphthyl substituted by lower alkyl, halo-lower alkyl, hydroxy, lower alkoxy, lower alkanoyloxy, halogen, cyano and/or by nitro. Aryl is preferably unsubstituted or is phenyl substituted as indicated above, and is especially phenyl.

Aryl-lower alkyl is preferably phenyl-lower alkyl and especially benzyl.

Aryl-lower alkenyl is preferably phenyl-lower alkenyl, especially phenylallyl or phenylvinyl (phenylethylene).

Lower alkoxycarbonyl-lower alkyl is, for example, propoxycarbonyl- or butoxycarbonyl-lower alkyl, preferably methoxycarbonyl-lower alkyl, and especially ethoxycarbonyl-lower alkyl, such as methoxycarbonyl- or ethoxycarbonyl-ethyl or-methyl.

Pharmaceutically acceptable acid addition salts of compounds of formula I are, for example, the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluenesulfonates or N-cyclohexylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, maleinates, fumarates, maleates, tartrates or citrates. Salts of compounds of formula I are, for example, the acid addition salts thereof, for example the pharmaceutically acceptable salts thereof with suitable mineral acids, such as hydrohalic acids, sulfuric acids or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

The compounds of formula I and the pharmaceutically acceptable salts thereof have valuable pharmacological properties. Those properties can be demonstrated in vivo for example using the model of adjuvant arthritis in the rat in accordance with I. Wiesenberg et at., Clin. Exp. Immunol. 78, 245 (1989) in a dosage range of from about 0.1 to about 10.0 mg/kg p.o. or i.p., especially from about 0.1 to about 3.0 mg/kg p.o. or i.p.

The compounds of formula I and their pharmaceutically acceptable salts can therefore be used for the treatment of diseases of the rheumatoid type. Those include especially rheumatoid arthritis, ankylosing spondylitis and other seronegative spondylarthritises, for example spondylarthritis in ulcerative colitis and Crohn's disease, and also reactive arthritises, collagen diseases, such as lupus erythematosus, degenerative rheumatic diseases, extra-articular rheumatic and pararheumatic diseases, for example gout and osteoporosis.

The invention relates especially to compounds of formula I wherein
$R_1$ and $R_5$ are $C_1$–$C_4$alkyl, $C_3$–$C_5$alk-2-en-1yl or $C_3$–$C_5$alk-2-yn-1yl,
$R_2$ and $R_3$ independently of one another are hydrogen or $C_1$–$C_4$alkyl or together are $C_1$–$C_4$alkylidene and
$R_4$ is $C_1$–$C_4$alkyl, $C_1$–$C_2$alkoxy, $C_3$–$C_5$alk-2-en-1-yl, $C_3$–$C_5$alk-2-yn-1-yl or phenyl-$C_1$–$C_2$alkyl,
and to the salts and tautomeric compounds and double-bond isomers thereof.

The invention relates more especially to compounds of formula I wherein
the radical $R_1$ is $C_3$–$C_5$alk-2-en-1-yl, such as allyl or methallyl, or $C_3$–$C_5$alk-2-yn-1-yl, such as prop-2-yn-1-yl,
$R_2$ and $R_3$ are both hydrogen or identical $C_1$–$C_4$alkyl groups, such as methyl groups, or $R_2$ and $R_3$ together are $C_1$–$C_4$alkylidene, such as methylene,
$R_4$ is $C_1$–$C_4$alkyl, such as methyl or ethyl, $C_1$–$C_2$alkoxy, such as methoxy or ethoxy, $C_3$–$C_5$alk-2-en-1-yl, such as allyl, methallyl or dimethylallyl, $C_3$–$C_5$ alk-2-yn-1-yl, such as prop-2-yn-1-yl, or phenyl-$C_1$–$C_2$alkyl, such as benzyl, and
$R_5$ is $C_3$–$C_5$alk-2-en-1-yl, such as allyl or methallyl, or $C_1$–$C_4$alkyl, such as methyl or ethyl,
and to the salts, especially the pharmaceutically acceptable salts, and tautomeric compounds and double-bond isomers thereof.

The invention relates most especially to compounds of formula I, wherein
$R_1$ is allyl, methallyl or prop-2-yn-1-yl,
$R_2$ and $R_3$ are both hydrogen or methyl, and R4 is allyl, dimethylallyl, prop-2-yn-1-yl or benzyl, and R5 is allyl or methyl, and to the salts, especially the pharmaceutically acceptable salts, and tautomeric compounds and double-bond isomers thereof.

The invention relates specifically to the compounds of formula I mentioned in the Examples, and to the salts, especially the pharmaceutically acceptable salts, thereof.

The novel compounds of formula I can be prepared in a manner known per se, by reacting a compound of formula II

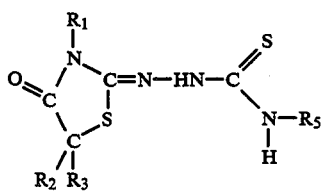

with a compound of formula III

R4—X    (III)

wherein X is a nucleofugal leaving group and $R_1$, $R_2$, $R_3$, $R_4$ and $R_5$ are as defined above.

The radical X in a compound of formula III is preferably halogen, for example chlorine, bromine or iodine, but may also be, for example, aliphatically or aromatically substituted sulfonyloxy, for example methylsulfonyloxy (mesylate) or 4-methylphenylsulfonyloxy (tosylate). As a further leaving group X it is also possible to use, for example, the trifluoroacetate group in a compound of formula III, R4—X.

The condensation of a compound of formula II with a compound of formula III is effected in the presence of a basic condensation agent, such as a tertiary organic base, such as a tri-lower alkylamine, for example triethylamine, a Hünig base or an organic nitrogen base, such as pyridine or quinoline in a temperature range of from 25° to 120° C., advantageously at the boiling temperature of the solvent.

There may be used as solvents protic and aprotic solvents, such as aliphatic halogenated hydrocarbons, for example dichloromethane, especially methylene chloride or aliphatic or cycloaliphatic ethers, such as tetrahydrofuran or dioxane. Toluene or ethanol may also be used as solvents.

Where appropriate, salts such as, for example, sodium or potassium iodide and/or catalytic amounts of dimethylaminopyridine may also be added as reaction accelerators.

The compounds of formula II and processes for the preparation thereof that are based on methods known per se are known and are described, for example, in GB-1 325 061, U.S. Pat. No. 4,697,020, DE-2 405 395 and DE-2 632 745 and as intermediates in the preparation of tumour-inhibiting medicinal active ingredients.

Compounds obtainable in accordance with the process can be converted in customary manner into other compounds of formula I.

Resulting salts can be convened into the free compounds in a manner known per se, for example by treatment with a base, such as an alkali metal hydroxide, a metal carbonate or a metal hydrogen carbonate, or with ammonia, or another salt-forming base mentioned at the beginning, or with an acid, such as a mineral acid, for example with hydrochloric acid, or another salt-forming acid mentioned at the beginning.

Resulting salts can be convened into different salts in a manner known per se, acid addition salts for example by treatment with a suitable metal salt, such as a sodium, barium or silver salt, of a different acid in a suitable solvent in which an inorganic salt being formed is insoluble and is therefore eliminated from the reaction equilibrium, and base salts by freeing the free acid and converting it into a salt again.

The compounds of formula I, including their salts, may also be obtained in the form of hydrates or may include the solvent used for crystallisation.

In view of the close relationship between the novel compounds in free form and in the form of their salts, hereinbefore and hereinafter any reference to the free compounds or their salts should be understood as including the corresponding salts or free compounds, respectively, as appropriate and expedient.

Resulting racemates can also be resolved into the optical antipodes by known methods, for example by recrystallisation from an optically active solvent, with the aid of micro-organisms or by reaction of the resulting diastereoisomeric mixture or racemate with an optically active auxiliary compound, for example according to the acidic, basic present in compounds of formula I or an optically active alcohol, to form mixtures of diastereoisomeric salts or functional derivatives, such as esters, separation of the same into the diasteroisomers from which the desired enantiomer can be freed in customary manner. Bases, acids and alcohols suitable for the purpose are, for example, optically active alkaloid bases, such as strychnine, cinchonine or brucine, or D- or L-(1-phenyl)ethylamine, 3-pipecoline, ephedrine, amphetamine and similar bases that can be obtained by synthesis, optically active carboxylic or sulfonic acids, such as quinic acid or D- or L-tartaric acid, D- or L-di-o-toluoyltartaric acid, or optically active alcohols, such as borneol or D- or L-(1phenyl)ethanol.

The invention relates also to those forms of the process according to which a compound obtainable as intermediate at any stage of the process is used as starting material and the remaining steps are carried out, or a starting material is used in the form of a salt or, especially, is foraged under the reaction conditions.

The invention relates also to the novel starting materials which have been developed specifically for the preparation of the compounds according to the invention, especially the group of starting materials that lead to the compounds of formula I mentioned at the beginning as being preferred, to the processes for their preparation and to their use as intermediates.

The pharmaceutical compositions according to the invention, which comprise the compound according to the invention or pharmaceutically acceptable salts thereof, are for enteral, such as oral, also rectal and parenteral, administration to (a) warm-blooded animal(s), and comprise the pharmacological active ingredient on its own or together with a pharmaceutically acceptable carrier. The daily dose of active ingredient is dependent on the age and individual condition as well as on the mode of administration.

The novel pharmaceutical compositions comprise, for example, from about 10% to about 80 %, preferably from about 20% to about 60%, active ingredient. Pharmaceutical compositions according to the invention for enteral and/or parenteral administration are, for example, those in unit dose form, such as dragées, tablets, capsules or suppositories, as well as ampoules. They can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and, if desired, processing the mixture or granules, if necessary with the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatin, tragacanth, methylcellulose and/or polyvinylpyrrolidone, if desired, disintegrators, such as the above-mentioned starches, also carboxymethyl starch, cross-linked polyvinylpyrrolidone, agar, alginic acid or a salt thereof, such as sodium alginate. Excipients are especially flow agents, flow conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical compositions are dry-filled capsules comprising gelatin, and also soft sealed capsules comprising gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycol, to which stabilisers may also have been added.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycol or higher alkanols. There may also be used gelatin rectal capsules, which comprise a combination of the active ingredient with a base material. Suitable base materials are, for example, liquid triglycerides, polyethylene glycol or paraffin hydrocarbons.

Suitable for parenteral administration are especially aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that comprise viscosity-increasing substances, for example sodium carboxymethylcellulose, sorbitol and/or dextran, and, optionally, stabilisers.

The invention relates also to the use of the compound of formula I, preferably in the form of pharmaceutical compositions. The dose of active ingredient is dependent on the species of warm-blooded animal, the age and the individual condition, as well as on the mode of administration. In normal cases, the approximate daily dose in the case of oral administration to a patient weighing about 75 kg is estimated to be from about 5 mg to about 1000 mg, especially approximately from 10 mg to 200 mg. The dose can be administered all at once or may be divided into several, for example from 2 to 4, individual doses. Pharmaceutical compositions in unit dose form thus comprise from about 5 mg to about 250 mg, especially from about 10 mg to 50 mg, of active ingredient.

The Examples that follow serve to illustrate the invention; temperatures are given in degrees Celsius, pressures in mbar.

EXAMPLE 1

With stirring at room temperature, 1.5 g of allyl bromide are added to 2.5 g of 1-(3-allyl-4-oxo-thiazolidin-2-ylidene)-4-methyl-thiosemicarbazone in 30 ml of methylene chloride and the resulting mixture is heated to the boiling point of the solvent and maintained under reflux for 4 hours. After cooling to room temperature, the solvent is removed using a rotary evaporator and the resulting residue is taken up in methylene chloride, washed with saturated sodium hydrogen carbonate solution, dried over magnesium sulfate and concentrated. Crystallisation from ether/petroleum ether and further recrystallisation from ethanol yield pure 1-(3-allyl-4-oxo-thiazolidin-2-ylidene)-4-methyl-thiosemicarbazonic acid allyl ester having a m.p. of 117°–118° C.

EXAMPLE 2

With stirring at room temperature, 0.75 g of dimethylallyl bromide is added in the presence of 0.5 g of triethylamine and a spatula tip of dimethylaminopyridine to 1.2 g of 1-(3-allyl-4-oxo-thiazolidin-2-ylidene)-4-methyl-thiosemicarbazone in 30 ml of tetrahydrofuran and the resulting mixture is heated to the boiling point of the solvent and maintained under reflux for 2 hours. After cooling to room temperature, the solvent is removed using a rotary evaporator and the resulting residue is taken up in methylene chloride, washed with water, dried over magnesium sulfate and concentrated. After crystallisation from methylene chloride/ether the crystals are dissolved in acetone, and 1 ml of 6N HCl in ethanol is added thereto. Filtration and drying at room temperature under a high vacuum yield 1-(3-allyl-4-oxo-thiazolidin-2-ylidene)-4-methyl-thiosemicarbazonic acid dimethylallyl ester hydrochloride having a m.p. of 119°–121° C.

EXAMPLE 3

Analogously to Example 1, 1.2 g of allyl bromide are added to 2.5 g of 1-(5,5-dimethyl- 3-methallyl-4-oxo-thiazolidin-2-ylidene )-4-allyl-thiosemicarbazone in 20 ml of methylene chloride and the mixture is then heated under reflux for 12 hours. After working up as described above under Example 1 the colourless oil is dissolved in ethanol, 1.5 ml of 6N HCl are introduced and ether is added. Filtration yields colourless crystals of 1-(5,5-dimethyl-3-methallyl-4-oxo-thiazolidin-2-ylidene)-4-allyl-thiosemicarbazonic acid allyl ester hydrochloride having a m.p. of 127°–129° C.

EXAMPLE 4

Analogously to Example 2, 1.6 g of 1-(5,5-dimethyl-3-methallyl-4-oxo-thiazolidin-2-ylidene)-4-allyl-thiosemicarbazone in 25 ml of methylene chloride and 0.7 g of methyl iodide are stirred at room temperature for 24 hours in the presence of 0.5 g of triethylamine. Then a further 0.5 g of methyl iodide and 0.3 g of triethylamine are added and the reaction mixture is boiled under reflux for 5 hours. Working up analogously to Example 2 and chromatography on silica gel with methylene chloride and crystallisation from ether/petroleum ether yield 1-(5,5-dimethyl-3-methallyl-4-oxo-thiazolidin-2-ylidene)-4-allyl-thiosemicarbazonic acid allyl ester hydrochloride in a diastereoisomeric ratio of 5:1, m.p. 98°–104° C.

EXAMPLE 5

Analogously to Example 2, 1.2 g of 1-(3-allyl-4-oxo-thiazolidin-2-ylidene)-4-methyl-thiosemicarbazone in 15 ml of methylene chloride and 0.8 g of methyl iodide are heated under reflux for 24 hours in the presence of 1.4 ml of triethylamine. Working up as described above in Example 2 and chromatography on silica gel yield 1-(3-ally-4-oxo-thiazolidin-2-ylidene)-4-methyl-thiosemicarbazonic acid methyl ester in a diastereoisomeric ratio of 3: 1, m.p. 127°–128° C.

EXAMPLE 6

Analogously to Example 2, 1.2 g of 1-(3-allyl-4-oxo-thiazolidin-2-ylidene)-4-methyl-thiosemicarbazone in 30 ml of tetrahydrofuran and 0.9 g of benzyl bromide are boiled under reflux for 5 hours in the presence of 0.5 g of triethylamine. After working up and crystallisation from methylene chloride/ether, the crystals are dissolved in acetone; 1 ml of 6N HCl in ethanol is added thereto, and crystals of 1-(3-allyl-4-oxo-thiazolidin-2-ylidene)-4-methyl-thiosemicarbazonic acid benzyl ester hydrochloride are obtained therefrom by filtration in a diastereoisomeric ratio of 7:1, m.p. 139°–141° C.

EXAMPLE 7

Analogously to Example 2, 1.2 g of 1-(3-allyl-4-oxo-thiazolidin-2-ylidene)-4-methyl-thiosemicarbazone in 30 ml of ethanol and 1.1 g of 2-bromomethyl-phenyl ether are boiled under reflux for 24 hours in the presence of 0.5 g of triethylamine and 0.3 g of sodium iodide. Working up and chromatography on silica gel with methylene chloride and crystallisation from ether yield crystals of 1-(3-allyl-4-oxo-thiazolidin-2-ylidene)-4-methyl-thiosemicarbazonic acid 2-phenoxyethyl ester having a m.p. of 106°–107° C.

EXAMPLE 8

Analogously to Example 2, 1.2 g of 1-(3-allyl-4-oxo-thiazolidin-2-ylidene)-4-methyl-thiosemicarbazone in 30 ml of tetrahydrofuran and 1.0 g of 3-phenyl-allyl 1-bromide are heated under reflux for 10 hours in the presence of 0.5 g of triethylamine and a spatula tip of dimethylaminopyridine. After working up and crystallisation from methylene chloride/ether, the crystals are dissolved in acetone; 1 ml of 6N HCl in ethanol is added thereto, and, after the addition of ether, colourless crystals of 1-(3-allyl-4-oxo-thiazolidin-2-ylidene)-4-methyl-thiosemicarbazonic acid styrene ester hydrochloride are obtained therefrom, m.p. 107°–110° C.

EXAMPLE 9

Analogously to Example 2, 2.4 g of 1-(3-allyl-4-oxo-thiazolidin-2-ylidene)-4-methyl-thiosemicarbazone in 30 ml of ethanol and 3.2 g of 3-(2,4-dihydroxy-3-propyl-acetophenon-4-yl)-propyl bromide are heated under reflux for 5 hours in the presence of 2.8 ml of triethylamine and 0.2 g of sodium iodide. Working up and recrystallisation once from ethanol yield crystals of 1-(3-allyl-4-oxo-thiazolidin-2-ylidene)-4-methyl-thiosemicarbazonic acid 3-(2,4-dihydroxy-3-propyl-acetophenon-4-yl)-propyl ester, m.p. 108°–110° C.

EXAMPLE 10

Analogously to Example 2, 2 g of 1-(3-allyl-4-oxo-thiazolidin-2-ylidene)-4-methyl-thiosemicarbazone and 0.7 ml of bromoethanol in 30 ml of ethanol are boiled under reflux for 15 hours in the presence of 1.4 ml of triethylamine, a catalytic amount of dimethylaminopyridine and 0.3 g of sodium iodide. Working up and chromatography on silica gel with ethyl acetate and crystallisation from ether yield crystals of 1-(3-allyl-4-oxo-thiazolidin-2-ylidene)-4-methyl-thiosemicarbazonic acid 2-hydroxyethyl ester in a diastereoisomeric ratio of 10:1, m.p. 103°–105° C.

EXAMPLE 11

Analogously to Example 2, 1.2 g of 1-(3-allyl-4-oxo-thiazolidin-2-ylidene)-4-methyl-thiosemicarbazone and 1.0 g of 4-fluorobenzyl bromide in 20 ml of tetrahydrofuran are boiled under reflux for 4 hours in the presence of 0.5 g of triethylamine and a spatula tip of dimethylaminopyridine. Working up and chromatography on silica gel with methylene chloride and crystallisation from methylene chloride/ether yield crystals of 1-(3-allyl-4-oxo-thiazolidin-2-ylidene)-4-methyl-thiosemicarbazonic acid 4-fluorobenzyl ester in a diastereoisomeric ratio of 6:1, m.p. 105°–106° C.

EXAMPLE 12

Analogously to Example 2, 1.2 g of 1-(3-allyl-4-oxo-thiazolidin-2-ylidene)-4-methyl-thiosemicarbazone and 1.1 g of 2-bromomethylbenzonitrile in 20 ml of tetrahydrofuran are boiled under reflux for 5 hours in the presence of 0.5 g of triethylamine and a spatula tip of dimethylaminopyridine. Working up and crystallisation from methylene chloride/ether yield colourless crystals of 1-(3-allyl-4-oxo-thiazolidin-2-ylidene)-4-methyl-thiosemicarbazonic acid 2-cyanobenzyl ester in a diastereoisomeric ratio of 4:1, m.p. 151°–152° C.

EXAMPLE 13

Analogously to Example 2, 1.2 g of 1-(3-allyl-4-oxo-thiazolidin-2-ylidene)-4-methyl-thiosemicarbazone and 0.7 g of propargyl bromide in 20 ml of tetrahydrofuran are boiled under reflux for 4 hours in the presence of 0.5 g of triethylamine and a spatula tip of dimethylaminopyridine. Working up and chromatography on silica gel with methylene chloride and crystallisation from methylene chloride/ether yield colourless crystals of 1-(3-allyl-4-oxo-thiazolidin-2-ylidene)-4-methyl-thiosemicarbazonic acid 1-propargyl ester in a diastereoisomeric ratio of 3:1, m.p. 91°–92° C.

EXAMPLE 14

Tablets, each comprising 10 mg of 1-(3-allyl-4-oxo-thiazolidin-2-ylidene)-4-methyl-thiosemicarbazonic acid allyl ester or a salt thereof, can be prepared as follows:

| Composition (10000 tablets) | |
|---|---|
| active ingredient | 100.0 g |
| lactose | 450.0 g |
| potato starch | 350.0 g |
| gelatin | 10.0 g |
| talcum | 60.0 g |
| magnesium stearate | 10.0 g |
| silicon dioxide (highly dispersed) | 20.0 g |
| ethanol | q.s. |

The active ingredient is mixed with the lactose and 292 g of potato starch, and the mixture is moistened with an ethanolic solution of the gelatin and granulated through a sieve. After drying, the remainder of the potato starch, the magnesium stearate, the talcum and the silicon dioxide are mixed in and the mixture is compressed to form tablets, each weighing 100.0 mg and comprising 10.0 mg of active ingredient; if desired the tablets may be provided with dividing notches for finer adaptation of the dose.

EXAMPLE 15

Hard gelatin capsules comprising 20 mg of active ingredient, 1-(3-allyl-4-oxo-thiazolidin-2-ylidene)-4-methyl-thiosemicarbazonic acid allyl ester or a salt thereof, can be prepared, for example, as follows:

| Composition (for 1000 capsules) | |
|---|---|
| active ingredient | 20.0 g |
| lactose | 240.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 300 mg of the resulting formulation.

EXAMPLE 16

Hard gelatin capsules comprising 100 mg of active ingredient, for example 1-(3-allyl-4-oxo-thiazolidin-2-ylidene)-4-methyl-thiosemicarbazonic acid allyl ester or a salt thereof, can be prepared, for example, as follows:

| Composition (for 1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 390 mg of the resulting formulation.

EXAMPLE 17

Film-coated tablets each comprising 50 mg of 1-(3-allyl-4-oxo-thiazolidin-2-ylidene)-4-methyl-thiosemicarbazonic acid allyl ester or a salt thereof, can be prepared, for example, as follows:

| Composition (for 1000 film-coated tablets) | |
|---|---|
| active ingredient | 50.0 g |
| lactose | 100.0 g |
| corn starch | 70.0 g |
| talcum | 10.0 g |
| calcium stearate | 2.0 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 240 mg) which are then film-coated with a solution of the hydroxypropylmethylcellulose and the shellac in methylene chloride; final weight of the film-coated tablet: 283 mg.

EXAMPLE 18

A 0.2% injection or infusion solution of 1-(3-allyl-4-oxo-thiazolidin-2-ylidene)-4-methyl-thiosemicarbazonic acid allyl ester or a salt thereof, can be prepared, for example, as follows:

| Composition (for 1000 ampoules) | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added and the solution is made up to 2500 ml with water. For the preparation of unit dose forms, 1.0 ml or 2.5 ml portions are introduced into glass ampoules, which then each comprise 2.0 or 5.0 mg of active ingredient, respectively.

EXAMPLE 19

A 1% ointment (o/w emulsion), comprising as active ingredient, for example, 1-(3-allyl-4-oxo-thiazolidin-2-ylidene)-4-methyl-thiosemicarbazonic acid allyl ester or a salt thereof, having the following composition:

| | |
|---|---|
| active ingredient | 1.0 g |
| cetyl alcohol | 3.0 g |
| glycerol | 6.0 g |
| methylparaben | 0.18 g |
| propylparaben | 0.05 g |

| | |
|---|---|
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water, q.s. ad | 100.0 g |

EXAMPLE 20

A 1% gel, comprising as active ingredient, for example, 1-(3-allyl-4-oxo-thiazolidin-2-ylidene)-4-methyl-thiosemicarbazonic acid allyl ester or a salt thereof, having the following composition:

| | |
|---|---|
| active ingredient | 1.0 g |
| Carbopol 934 P | 1.0 g |
| glycerol | 3.0 g |
| isopropanol | 25.0 g |
| Softigen ® 767 | 0.2 g |
| demin. water, q.s. ad | 100.0 g |

EXAMPLE 21

In a manner analogous to that described in the above Examples 14 to 20, it is also possible to prepare pharmaceutical compositions comprising a different compound of formula I or a pharmaceutically acceptable salt thereof.

What is claimed is:

1. A compound of formula I

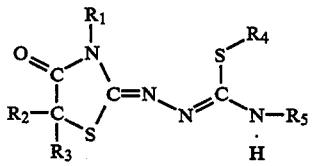

wherein
$R_1$ and $R_5$ are lower alkyl, lower alk-2-en-1-yl or lower alk-2-yn-1-yl,
$R_2$ and $R_3$ independently of one another are hydrogen or lower alkyl or together are lower alkylidene and
$R_4$ is lower alkyl, lower alkoxy, lower alk-2-en-1-yl, lower alk-2-yn-1-yl, aryl-lower alkyl, aryl-lower alkenyl or lower alkoxycarbonyl-lower alkyl,
or a salt or tautomeric compound or double-bond isomer thereof.

2. A compound according to claim 1 of formula I wherein
$R_1$ and $R_5$ are $C_1$-$C_4$alkyl, $C_3$-$C_5$alk-2-en-1-yl or $C_3$-$C_5$alk-2-yn-1-yl,
$R_2$ and $R_3$ independently of one another are hydrogen or $C_1$-$C_4$alkyl or together are $C_1$-$C_4$alkylidene and
$R_4$ is $C_1$-$C_4$alkyl, $C_1$-$C_2$alkoxy, $C_3$-$C_5$alk-2-en-1-yl, $C_3$-$C_5$alk-2-yn-1-yl or phenyl-$C_1$-$C_2$alkyl,
or a salt or tautomeric compound or double-bond isomer thereof.

3. A compound according to claim 1 of formula I wherein
the radical $R_1$ is $C_3$-$C_5$alk-2-en-1-yl, or $C_3$-$C_5$alk-2-yn-1-yl,
$R_2$ and $R_3$ are both hydrogen or identical $C_1$-$C_4$alkyl groups, or $R_2$ and $R_3$ together are $C_1$-$C_4$alkylidene,
$R_4$ is $C_1$-$C_4$alkyl, $C_1$-$C_2$alkoxy, $C_3$-$C_5$alk-2-en-1-yl, $C_3$-$C_5$alk-2-yn-1-yl, or phenyl-$C_1$-$C_2$alkyl, and
$R_5$ is $C_3$-$C_5$alk-2-en-1-yl, or $C_1$-$C_4$alkyl,
or a pharmaceutically acceptable salt or tautomeric compound or double-bond isomer thereof.

4. A compound selected from the group consisting of
1-(3-allyl-4-oxo-thiazolidin-2-ylidene)-4-methylthiosemicarbazonic acid allyl ester,
1-(3-allyl-4-oxo-thiazolin-2-ylidene)-4-methyl-thiosemicarbazonic acid dimethylallyl ester,
1-(5,5-dimethyl-3-methally-4-oxo-thiazolidin-2-ylidene)-4-allyl-thiosemicarbazonic acid ally ester,
1-(5,5-dimethyl- 3-methallyl-4-oxo-thiazolidin-2-ylidene)-4-alkyl-thiosemicarbazonic acid alkyl ester,
1-(3-allyl-4-oxo-thiazolidin-2-ylidene)-4-methyl-thiosemicarbazonic acid benzyl ester,
1-(3-allyl-4-oxo-thiazolidin-2-ylidene)-4-methyl-thiosemicarbazonic acid methyl ester,
1-(3-allyl-4-oxo-thiazolidin-2-ylidene)-4-methyl-thiosemicarbazonic acid 2-phenoxyethyl ester,
1-(3-allyl-4-oxo-thiazolidin-2-ylidene)-4-methyl-thiosemicarbazonic acid styrene ester,
1-(3-allyl-4-oxo-thiazolidin-2-ylidene)-4-methyl-thiosemicarbazonic acid 3-(2,4-dihydroxy-3-propyl-acetophenon-4-yl)-propyl ester,
1-(3-allyl-4-oxo-thiazolidin-2-ylidene)-4-methyl-thiosemicarbazonic acid 2-hydroxyethyl ester,
1-(3-allyl-4-oxo-thiazolidin-2-ylidene)-4-methyl-thiosemicarbazonic acid 4-fluorobenzyl ester,
1-(3-allyl-4-oxo-thiazolidin-2-ylidene)-4-methyl-thiosemicarbazonic acid 2-cyanobenzyl ester, and
1-(3-allyl-4-oxo-thiazolidin-2-ylidene)-4-methyl-thiosemicarbazonic acid 1-propargyl ester,
or a pharmaceutically acceptable salt thereof.

5. A pharmaceutical composition for the treatment of a rheumatoid type disease comprising an effective rheumatoid type disease treating effective amount of a compound according to claim 1, in the free form or in the form of a pharmaceutically acceptable salt and a pharmaceutically acceptable carrier.

6. A pharmaceutical composition for the treatment of a rheumatoid type disease comprising an effective rheumatoid type disease treating effective amount of a compound according to claim 3, in the free form or in the form of a pharmaceutically acceptable salt and a pharmaceutically acceptable carrier.

7. A method of treating a rheumatoid type disease in an animal in need thereof comprising administering to said animal a rheumatoid type disease treating effective amount of a compound of claim 1 in the free form or in the form of a pharmaceutically acceptable salt.

8. A method of treating a rheumatoid type disease in an animal in need thereof comprising administering to said animal a rheumatoid type disease treating effective amount of a compound of claim 4 in the free form or in the form of a pharmaceutically acceptable salt.

* * * * *

UNITED STATES PATENT AND TRADEMARK OFFICE
CERTIFICATE OF CORRECTION

PATENT NO. : 5,338,746

DATED : August 16, 1994

INVENTOR(S) : Martin Missbach

It is certified that error appears in the above-indentified patent and that said Letters Patent is hereby corrected as shown below:

In claim 4, column 12, line 18, change "ally ester" to --allyl ester--

In claim 6, column 12, line 50, change "3" to --4--

Signed and Sealed this

Eleventh Day of October, 1994

Attest:

Attesting Officer

BRUCE LEHMAN

Commissioner of Patents and Trademarks